(12) United States Patent
Gil et al.

(10) Patent No.: US 10,335,505 B2
(45) Date of Patent: Jul. 2, 2019

(54) STERILIZATION DEVICE FOR INCISION AND WOUND SITES UTILIZING LOW INTENSITY UV-C RADIATION AND OZONE (71) Applicant: HEPCO HOLDINGS, LLC, Seminole, FL (US)

(72) Inventors: Patricia Carol Gil, Belleair Bluffs, FL (US); Asher Gil, Belleair Bluffs, FL (US); Daniel Gil, Madison, WI (US)

(73) Assignee: Hepco Holdings, LLC, Seminole, FL (US)

( * ) Notice: Subject to any disclaimer, the term of this patent is extended or adjusted under 35 U.S.C. 154(b) by 69 days.

(21) Appl. No.: 15/683,921

(22) Filed: Aug. 23, 2017

(65) Prior Publication Data
US 2019/0060495 A1 Feb. 28, 2019

(51) Int. Cl.
A61L 2/10 (2006.01)
A61L 2/20 (2006.01)

(52) U.S. Cl.
CPC ............. A61L 2/10 (2013.01); A61L 2/202 (2013.01); A61L 2202/14 (2013.01); A61L 2202/21 (2013.01)

(58) Field of Classification Search
CPC ........ A61L 2/10; A61L 2/202; A61L 2202/14; A61N 5/0624
See application file for complete search history.

(56) References Cited

U.S. PATENT DOCUMENTS

| 2,569,079 | A | 10/1950 | Special |
| 5,446,289 | A | 8/1995 | Shodeen et al. |
| 6,146,588 | A | 11/2000 | Deighton |
| 7,090,649 | B2 * | 8/2006 | Kang ................. A61H 23/0245 601/15 |
| 7,344,272 | B2 | 3/2008 | Cooper et al. |
| 7,875,869 | B1 | 1/2011 | Shadan |
| 7,960,706 | B2 | 6/2011 | Ullman |
| 8,241,565 | B1 | 8/2012 | Abdul |
| 8,624,202 | B2 | 1/2014 | Gil et al. |
| 8,784,731 | B2 | 7/2014 | Gil et al. |
| 2003/0088297 | A1 | 5/2003 | Stoppler |
| 2003/0163068 | A1 * | 8/2003 | Kang ................. A61H 23/0245 601/15 |
| 2004/0052702 | A1 | 3/2004 | Shuman |
| 2004/0116984 | A1 * | 6/2004 | Spooner ............... A61N 5/0614 607/88 |
| 2004/0262241 | A1 | 12/2004 | Socha |
| 2005/0013729 | A1 | 1/2005 | Brown-Skrobot |
| 2005/0263015 | A1 | 12/2005 | Mulgrew |

(Continued)

Primary Examiner — Christopher A Flory
(74) Attorney, Agent, or Firm — Larson & Larson, P.A.; Frank Liebenow; Justin P. Miller (57) ABSTRACT A sterilization system uses ultraviolet radiation and ozone to eradicate deadly pathogens to sterilize wound/incision sites. The sterilization system offers a safe sterilization method prior to or after surgery and/or closure wounds/incisions. The sterilization system has ultraviolet emitters that emit ultraviolet light in wavelengths that kill pathogens and in wavelengths that produce ozone at the sites, therefore killing/disabling several hard-to-kill pathogens. The sterilization system has surface detectors to enable ultraviolet emission only when the system is properly seated against the skin so as to protect from unwanted radiation from the ultraviolet light.

18 Claims, 4 Drawing Sheets

(56) References Cited

U.S. PATENT DOCUMENTS

| | | | |
|---|---|---|---|
| 2006/0047329 A1* | 3/2006 | Krespi | A61N 5/0603 607/86 |
| 2006/0089687 A1* | 4/2006 | Spooner | A61N 5/0614 607/88 |
| 2006/0206173 A1* | 9/2006 | Gertner | A61N 5/0616 607/88 |
| 2007/0075268 A1 | 4/2007 | Harris | |
| 2007/0164232 A1 | 7/2007 | Rolleri et al. | |
| 2007/0185553 A1* | 8/2007 | Kennedy | A61N 5/0616 607/100 |
| 2007/0192986 A1 | 8/2007 | Garcia et al. | |
| 2007/0208395 A1 | 9/2007 | Leclerc et al. | |
| 2007/0274879 A1 | 11/2007 | Millikin | |
| 2008/0308748 A1 | 12/2008 | Burrows | |
| 2009/0065716 A1 | 3/2009 | Ullman | |
| 2009/0143842 A1* | 6/2009 | Cumbie | A61N 5/0616 607/88 |
| 2009/0169426 A9 | 7/2009 | Toepfer et al. | |
| 2009/0240310 A1* | 9/2009 | Kennedy | A61N 5/0616 607/89 |
| 2010/0049177 A1* | 2/2010 | Boone, III | A61H 9/0057 606/9 |
| 2010/0076526 A1* | 3/2010 | Krespi | A61N 5/0603 607/88 |
| 2010/0179469 A1* | 7/2010 | Hammond | A61N 5/0603 604/20 |
| 2011/0037002 A1* | 2/2011 | Johnson | A61N 5/0613 250/504 R |
| 2011/0240883 A1 | 10/2011 | Ullman | |
| 2012/0045363 A1 | 2/2012 | Gil | |
| 2012/0310141 A1* | 12/2012 | Kornfield | A61F 9/008 604/20 |
| 2012/0328474 A1 | 12/2012 | Campagna | |
| 2013/0101461 A1 | 4/2013 | Gil et al. | |
| 2014/0264076 A1 | 9/2014 | Bettles | |
| 2014/0277299 A1* | 9/2014 | Intintoli | A61N 5/0616 607/94 |
| 2015/0238774 A1* | 8/2015 | Anderson | A61F 13/00063 604/20 |
| 2015/0359668 A1* | 12/2015 | Kornfield | A61F 9/008 604/20 |
| 2016/0101202 A1* | 4/2016 | Gil | A61L 2/202 422/186.3 |
| 2016/0129279 A1* | 5/2016 | Ferolito | A61N 5/0618 607/89 |
| 2016/0158575 A1* | 6/2016 | Levatter | A61N 5/0616 607/88 |
| 2016/0287896 A1* | 10/2016 | Anderson | A61F 13/00063 |

* cited by examiner

STERILIZATION DEVICE FOR INCISION AND WOUND SITES UTILIZING LOW INTENSITY UV-C RADIATION AND OZONE

CROSS-REFERENCE TO RELATED APPLICATION

This application claims the benefit of U.S. provisional application No. 62/377,913 filed on Aug. 22, 2016 and is a continuation-in-part of U.S. patent application Ser. No. 14/872,387 filed on Oct. 1, 2015, the disclosure of which are incorporated by reference.

FIELD

This invention relates to the field of medicine and more particularly to a system for sterilizing (e.g. the skin) of a portion of a patient.

BACKGROUND

The rising problem of antibiotic resistance has led to fears that medicine will return to the situation of a century ago when extensive wounds and surgery often led to death due to uncontrollable infection. These fears have in turn spurred a major research effort to find alternative antimicrobial approaches which, it is hypothesized, will kill resistant micro-organisms while being unlikely to cause resistance to develop to themselves. At the present time many international research efforts to discovery new antimicrobials are underway. Recently, the emphasis is on how to take precautions against creating, and if possible eliminate multidrug resistance in concert with exploring new methods to kill pathogenic microorganisms. Karen et al. in "Tackling antibiotic resistance," Bush K, *Nat Rev Microbiol*. 2011 Nov. 2; 9(12):894-6, recently pointed out that the investigation of novel non-antibiotic approaches, which can prevent and protect against infectious diseases should be encouraged, and should be looked upon as a high-priority for research and development projects.

The best known source of sterilization is UV-C radiation (wavelength: 200-280 nm). Among this wavelength range, the optimum range of 250-270 nm has the optimum potential ability to inactive microorganisms because it is strongly and mainly absorbed by nucleic acids of microbial cells and, therefore is the most lethal range of wavelengths.

The bactericidal mechanism of UV-C is to cause damage to their RNA and DNA, which often leads to the formation of dimers between pyrimidine residues in the nucleic acid strands. The consequence of this modification is that the production of cyclobutane pyrimidine dimers (CPDs) causes deformation of the DNA molecule, which might cause defects in cell replication and lead to cell death afterwards.

It is well known that prolonged and repeated exposure to UV irradiation can damage host cells and be particularly hazardous to human skin. As to long-term UVC irradiation of human skin, it is also known to have potential carcinogenicity. When UVC irradiation is applied to treat localized infections, one must consider the possible side-effects of UVC delivered at effective antimicrobial fluences on normal mammalian cells and tissue. The safety issue of UVC germicidal treatment requires that the pathogenic microbe is selectively eradicated while the normal tissue cells are spared.

It has been found that no significant adverse effects were induced in human primary corneal epithelial cells when the cells were exposed to 1.93 mJ/cm2 UVC (265 nm), which induced 100% inhibition of growth of all the bacterial species cultured on agar plates. UVC has been used to reduce pathogen contamination of platelet concentrates. The results showed UVC inactivated more than 4 log 10 Gram-positive *S. aureus, Bacillus cereus* and *S. epidermidis*, and Gram-negative *E. coli, P. aeruginosa* and *Klebsiella pneumoniae*.

Most of the experimental results mentioned above suggest that UVC at appropriate fluences does not cause significant damages to host cells and tissues. However, UVC irradiation still has potential to induce nonspecific damage. Studies demonstrated that the DNA of mammalian cells could indeed be damaged by UVC at its effective antimicrobial fluences. Fortunately however, at the same time, the DNA repairing enzymes of the host cells could rapidly repair the damaged DNA. In addition, to minimize the UVC-induced non-specific damage, the intact skin around the area to be treated could be shielded from UVC illumination. On the other hand, application of UVC is limited in some special locations due to its detrimental effects such as infections of the eyes.

A study presented by Taylor et al., reported that the mean bacterial CFU in joint arthroplasty surgical wounds was reduced by 87% with 0.1 mW/cm2 (P<0.001) and 92% with 0.3 mW/cm2 (P<0.001) of UVC. Thai et al. used UVC irradiation to treat cutaneous ulcers infected with MRSA. In all three patients, UVC treatment reduced the bacterial burden in wounds and promoted wound healing. Two patients had complete wound closure following 1 week of UVC treatment. Another trial was carried out by the same investigators in 22 patients with chronic ulcers manifesting at least two signs of infection and critically colonized with bacteria. The patients received a single UVC treatment and demonstrated significantly reductions of the bacterial burden. In a study, thirty patients with mild-to-moderate toenail onychomycosis were used to treat with UVC. Improvement by at least 1 measurement point was achieved in 60% of patient at 16-week follow-up compared with baseline. There were some unusual and slight side effects such as temporary mild eythema of the treated toe. In addition to the inactivation of microbial cells in the cutaneous wound, UVC exposure is beneficial for wound healing by promoting the expression of basic fibroblast growth factor (bFGF) and transforming growth factor, although the exact mechanisms of UVC for wound healing is still unclear. Others have investigated the prophylactic efficacies of UVC irradiation in 18 cases of catheter exit-site infections. Although five cases remained unchanged, ten cases (55%) became culture negative and a further three cases showed a microbial decrease.

In summary, it has been known during the past one-hundred years that UVC irradiation is highly bactericidal; however, using UVC illumination for the prophylaxis and treatment of localized infections is still at very early stages of development. Most of the studies are limited to in vitro and ex vivo levels, while in vivo animal studies and clinical studies are much rarer. A major advantage of using UVC over antibiotics is that UVC can eradicate resistant and pathogenic microorganisms much more rapidly without any systemic side-effects. UVC may also be much more cost effective than the commonly used antibiotics.

What is needed is a system that will expose a locale of a human (or animal) to UVC and ozone to reduce or eliminate pathogens.

SUMMARY

The disclosed system for directly radiating a wound generally relates to using UV-C radiation in combination with ozone to eradicate deadly pathogens (germs and viruses, spores and fungus) to sterilize wound/incision sites. The system for directly radiating a wound more particularly relates to a device that can be used both prior to surgery and prior to closing an incision following surgery. This the system for directly radiating a wound is activated by a person placing the head of the device above the wound/incision site and activating the sterilization process by, for example, stepping on a foot control device. Once activated, the device will activate UV-C bulbs that emit UV-C radiation and ozone to will sterilize the wound/incision site. Both UV-C radiation and ozone are provided to kill/neutralize certain pathogens that are not killed/neutralized by ultraviolet light alone. The wound, incision site, or pre-incision site will be exposed for a time specified by and controlled by, for example, an electronic timer or programmatic delay.

In one embodiment, a system for directly radiating skin is disclosed including an enclosure having one or more ultraviolet emitters housed therein and configured to selectively emit ultraviolet light from the housing onto a surface where the ultraviolet light produces ozone at the surface. There is a mechanism for detecting contact with the surface and a mechanism for connecting a source of power to the one or more ultraviolet emitters for a period of time responsive to detecting that the enclosure is positioned against the surface.

In another embodiment, a method of radiating skin is disclosed including providing a system that selectively emits ultraviolet light. The system has one or more skin contact detectors. The system that selectively emits ultraviolet light is placed against skin, thereby the one or more skin contact detectors detecting contact with the skin. Responsive to detecting the system being placed against the skin, the system that selectively emits ultraviolet light emits the ultraviolet light and the ultraviolet light and produces ozone at the skin. After delaying for a period of time, the system that selectively emits ultraviolet light is disabled, thereby stopping emission of the ultraviolet light and stopping production of the ozone.

In another embodiment, a system for radiating skin is disclosed including an enclosure having therein one or more ultraviolet emitters that are covered by a filter. The filter passes ultraviolet light from the one or more ultraviolet emitters. The one or more ultraviolet emitters are configured to emit ultraviolet light from the housing, through the filters, and onto a surface of the skin where ozone is produced by the ultra violet light. There is a mechanism for detecting contact with the surface of the skin that is configured to prevent the one or more ultraviolet emitters from emitting the ultraviolet light until contact is made with the surface of the skin and there is a timer that is configured to connect a source of power to the one or more ultraviolet emitters for a period of time responsive to the contact being made with the surface of the skin.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Throughout this description, the term "sterilize" is used to describe the act of killing pathogens. Although "sterile" often refers to something being void of pathogens, the term "sterilize" is the process of destroying (killing or disabling) microorganisms, as it is anticipated that most or all pathogens will be destroyed, though depending on UVC dosage and ozone exposure, it is anticipated that not all pathogens will be destroyed with each use of the described apparatus.

Throughout this description, the system is described as a system to directly radiate skin (e.g. a wound) where the skin is, for example, an area in which an incision will be made, an incision that was made during an operation, either an open incision or a closed incision—closed by, for example, stitches, etc. The wound is also anticipated to be a wound that has occurred by accident (e.g., an abrasion or dog bite) or due to an ailment such as a bed sore, etc. There is no limitation on how the described system is used. For example, it is fully anticipated that the described system be used to radiate an area of skin where there is no wound, for example, before an incision is made, etc.

Ultraviolet radiation is well known for its ability to eradicate deadly pathogens. However, the time required to do so is a serious consideration as extended exposure to UV-C has the potential of being harmful to tissue/skin around wound/incision sites. The system for directly radiating a wound herein described circumvents the potential dangers of exposure by reducing the time necessary for eradication of deadly pathogens by incorporating a short burst of ozone. The ozone acts as a catalyst to destroy the protective membrane (shell) that surrounds certain pathogens that are capable of causing an infection that is capable of leading to death. By reducing the time needed to expose the surrounding skin the system for directly radiating a wound reduces potential dangers of exposure to UV-C and at the same time reduces the time necessary for the sterilization process.

The invention generally relates to using ultraviolet radiation in combination with ozone to eradicate deadly pathogens (germs and viruses, spores and fungus) to sterilize, for example, a wound/incision site. The invention more particularly relates to a system for directly radiating a wound that is used both prior to surgery and prior to closing an incision following surgery. This system for directly radiating a wound is activated, for example, by a person placing the head of the device above the wound/incision and initiating UV-C bulbs to therefore emit ozone which will sterilize (kill a number of pathogens) at the wound/incision site using UV-C radiation and ozone. The wound/incision site will be exposed for a time specified by and controlled by an electronic timer that begins by, for example, operating a switch or a foot control device. Once activated, the system for directly radiating a wound produces both UV-C and ozone on the wound/incision area. For example, the period of time is from 5 to 100 seconds, which is sufficient to kill/disable pathogens but short enough to prevent damage to the skin.

In a preferred embodiment, the system for directly radiating a wound described herein incorporates a protective shield that is designed to direct the UV-C plus ozone light to the wound/incision site and at the same time protecting the user from unnecessary exposure the both UV-C and ozone.

In a preferred embodiment, the system for directly radiating a wound incorporates safety sensors to ensure that the device is activated only when it is in optimal position. This prevents the system for directly radiating a wound from emitting UV-C until it is in position (e.g. against the patient's skin).

Figure 1:
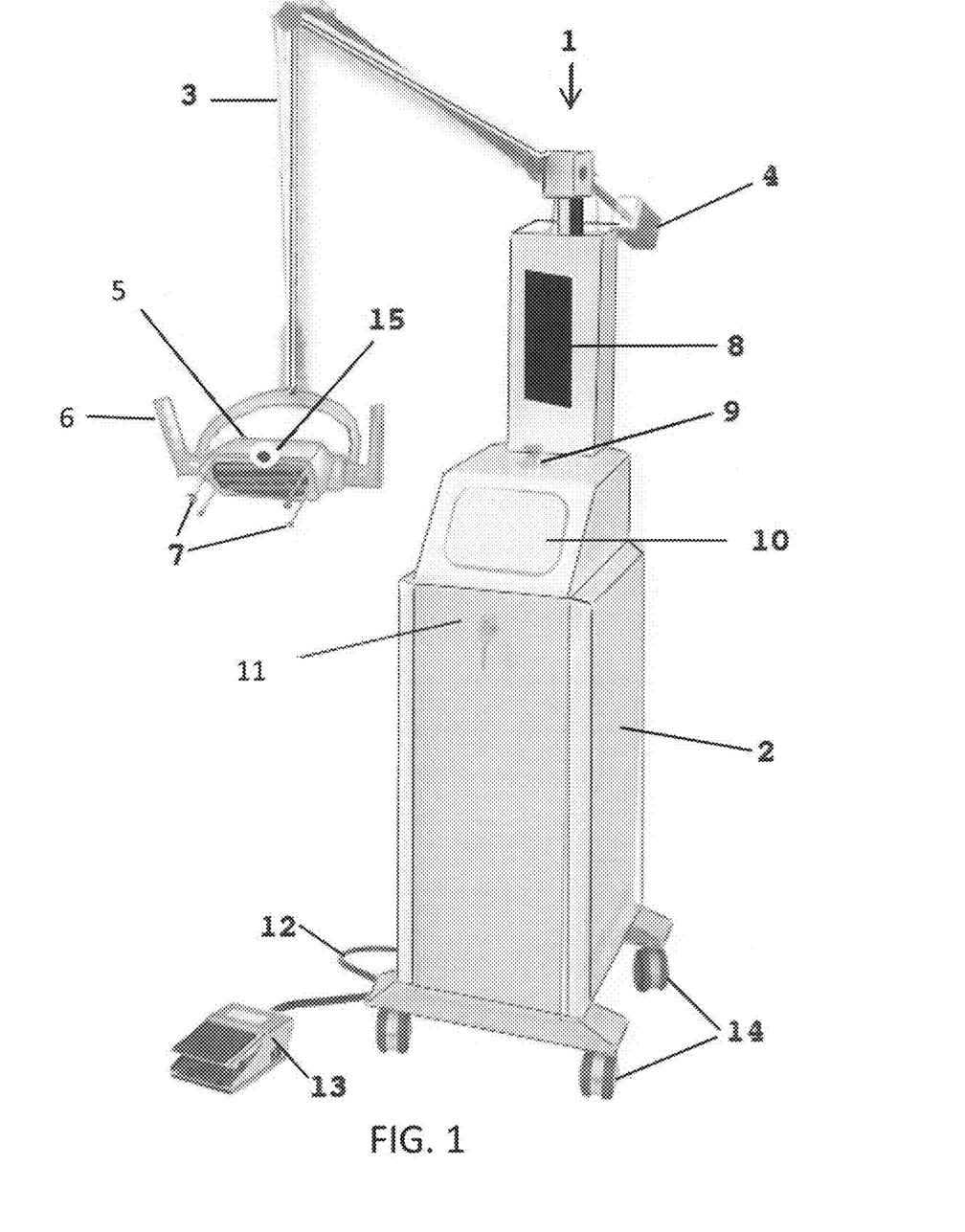
FIG. 1 is a perspective view of a system for directly radiating skin.

Referring to FIG. 1, a perspective view of the system for directly radiating skin 1 is shown in an exemplary physical embodiment. The system for directly radiating skin 1 includes, for example, a base 2 for housing electrical components (see FIG. 4), an articulating arm 3 hingedly connected to the base, an optional counter-weight 4, a head 5 having there within the ultraviolet emitters 70 (see FIG. 4) that also emit ozone, optional handles 6, position sensors 7, a computer display 8, indicator light 9 (e.g. LEDs), a control panel 10, an optional lock 11, electrical cord 12, an optional foot control 13, wheels 14 and a camera 15. Although shown as a floor-based system, it is fully anticipated that system for directly radiating skin 1 be embodied in a hand-held device including the head 5 with all controls, ultraviolet emitters 70, etc., contained there within the head 5.

Figure 4:
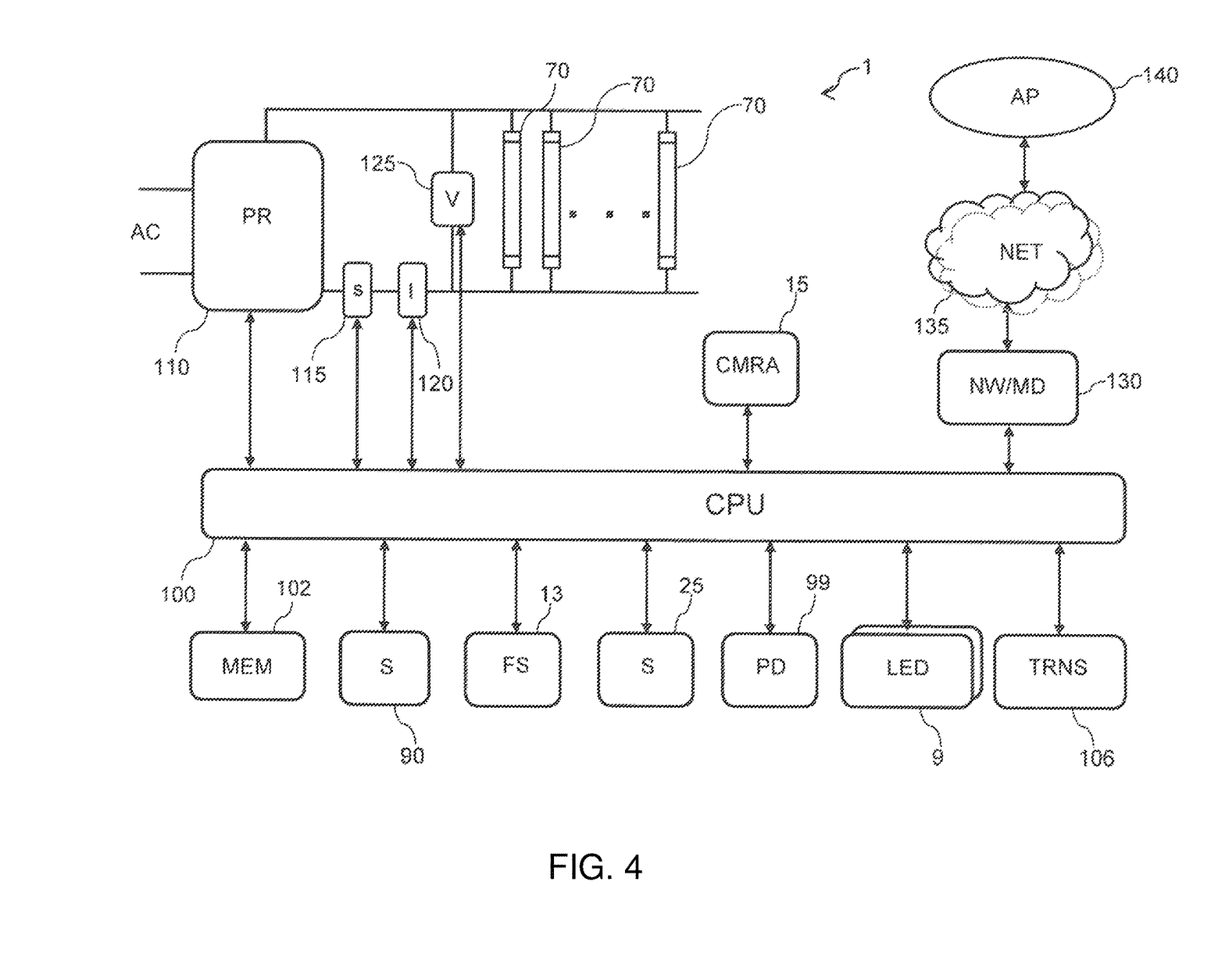
FIG. 4 is a schematic diagram of the system for directly radiating skin.

The ultraviolet emitters 70 preferably emit ultraviolet radiation at wavelengths that kill/disable pathogens and also generate ozone, as ozone is a gas that is known to aid in the destruction/disablement of certain pathogens that may not be killed solely by ultraviolet light. For example, the ultraviolet emitters 70 emit at a wavelength of around 254 nm to kill/disable many pathogens and emit at a wavelength of 185 nm to generate ozone to kill/disable some hard to kill pathogens such as MRSA, etc. In such, it is fully anticipated that a single ultraviolet emitter 70 emit both wavelengths of radiation or some of the ultraviolet emitters 70 emit at one wavelength of radiation and other of the ultraviolet emitters 70 emit at another wavelength of radiation. There is no limitation on the types and configuration of ultraviolet emitters 70 as long as the requisite wavelengths of radiation are emitted and directed towards the wound to kill/disable pathogens in the area of the wound.

Figure 2:
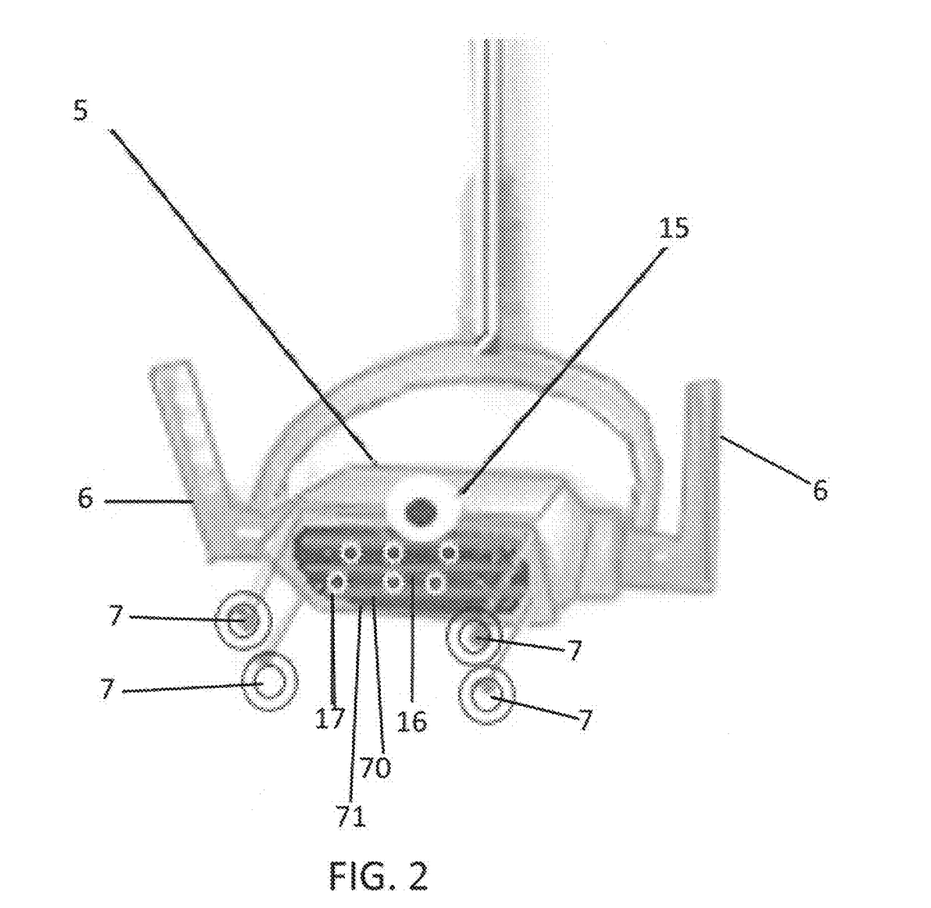
FIG. 2 is a perspective view of a device head showing some of the components incorporated in the head of the system for directly radiating skin.

Referring to FIG. 2 is a perspective view of the system for directly radiating skin 1 showing details of the head 5, position sensors 7, handles 6, and one or more ultraviolet emitting bulbs 70. In some embodiments, there are additional LEDs 17 to shed light on the patient while positioning the head 5. The head 5 includes one or more ultraviolet emitters 70 (e.g. ultraviolet emitting tubes, ultraviolet emitting light emitting diodes or LEDs, etc.) and, for protection from electrical shock, it is preferred that the one or more ultraviolet emitting bulbs 70 be protected by a cover 71 that is made of a sturdy material that efficiently passes ultraviolet light in both the wavelengths that are known to kill/neutralize pathogens (e.g. 254 nm) and wavelengths that are known to create the requisite ozone ($O_3$) (e.g. 185 nm). In some embodiments, the cover 71 comprises fused silica. In a less preferred embodiment, the cover comprises fused quartz.

Figure 3:
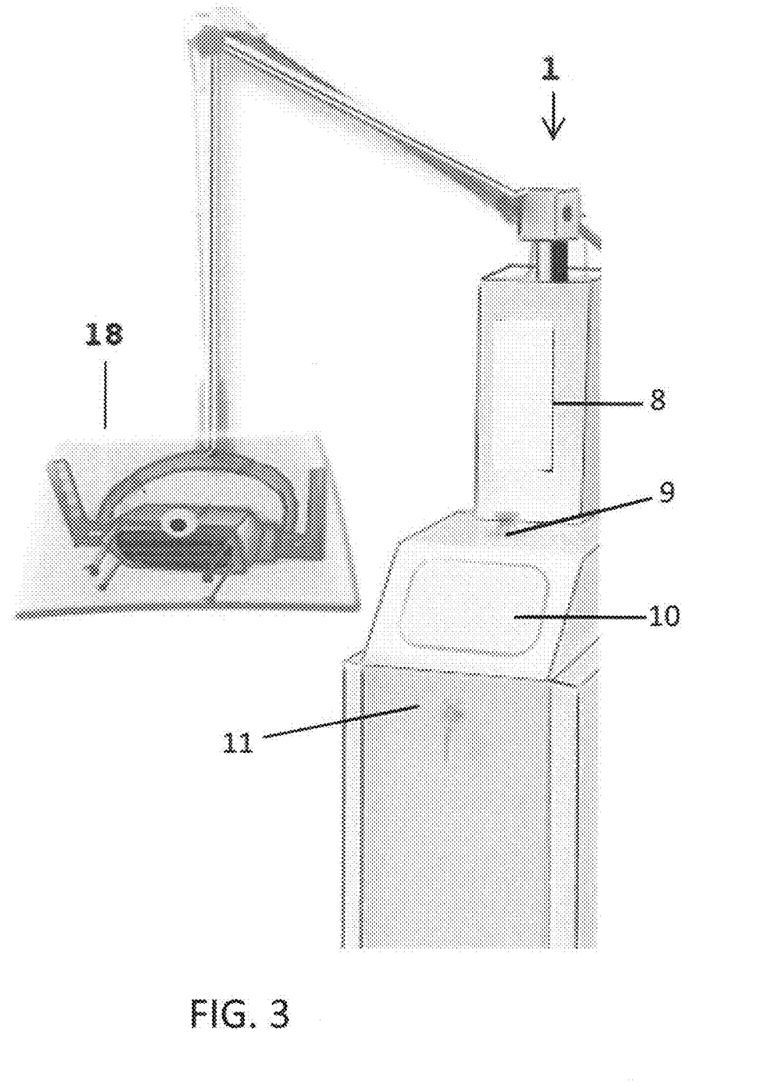
FIG. 3 is a perspective view of the device head showing a protective shield.

Referring to FIG. 3 is a perspective view of the system for directly radiating skin 1 showing a protective shield 18. The protective shield 18 is made of a pliable material such as rubber or soft plastic that, when pressed against a patient's skin, conforms to contours of the patient's skin, thereby sealing against the patient's skin and reducing emissions of ultraviolet light from the one or more ultraviolet emitting bulbs 70, as such emissions have the potential to affect the technician's and doctor's eyesight. As it is difficult to see ultraviolet light (human eyes typically do not visualize ultraviolet light), the optional LEDs 17 provide visible light emanating from the head 5, beneath the protective shield 18. Therefore, should the protective shield 18 not seal properly against the patient's skin, the technician/doctor is able to see the visible light and can adjust the head 5 or stop operation of the one or more ultraviolet emitting bulbs 70.

Referring to FIG. 4, block diagram showing an exemplary electrical sub-system 96 of the exemplary system for directly radiating skin 1 is shown. This is an example of one implementation, utilizing a processor 100 to control operation of the system for directly radiating skin 1. There are many other implementations anticipated, with or without the use of a processor 100 or processing element 100.

The exemplary processor-based sub-system 96 is shown having a single processor 100, though any number of processors 100 is anticipated. Many different computer architectures are known that accomplish similar results in a similar fashion and, again, the present invention is not limited in any way to any particular processor 100 or computer system. In this exemplary processor-based sub-system 96, the processor 100 executes or runs stored programs that are generally stored for execution within a memory 102. The processor 100 is any processor or a group of processors, for example an Intel 80051 or processors that are known as Programmable Logic Controllers (PLCs). The memory 102 is connected to the processor as known in the industry and the memory 102 is any memory or combination of memory types suitable for operation with the processor 100, such as SRAM, DRAM, SDRAM, RDRAM, DDR, DDR-2, flash, EPROM, EEPROM, etc. The processor 100 is connected to various devices (e.g. sensors, relays, lights, etc.) by any known direct or bus connection.

For AC powered operation, AC power is conditioned and regulated by a power regulator 110, as known in the industry. The power regulator 110 provides power for operation of the one or more devices that emit ultraviolet radiation 70, for the processor 100, and for any other component of the processor-based sub-system 96. In this example, one or more devices that emit ultraviolet radiation 70 are ultraviolet emitting bulbs 70, similar in operation to small florescent bulbs, though the present invention is not limited to any particular devices that emit ultraviolet radiation 70; and ultraviolet emitting LEDs or any ultraviolet emitter is anticipated. In general, such devices that emit ultraviolet radiation 70 operate at a specific voltage and draw a typical amount of current per specifications from suppliers of such devices that emit ultraviolet radiation 70. As the devices that emit ultraviolet radiation 70 age or fail, such aging or failure is detected by monitoring of the current and/or voltage provided to the devices that emit ultraviolet radiation 70 by one or more sensors 120/125. For example, one sensor 120 monitors voltage over the devices that emit ultraviolet radiation 70 and another sensor 125 monitors current to/from the devices that emit ultraviolet radiation 70. Outputs of the sensors 120/125 are connected to the processor 100. Upon detection of a failed or aging devices that emit ultraviolet radiation 70, the processor 100 signals such aging or failure by eliminating one or more lamps or LEDs 104, changing the color of one or more lamps or LEDs 104, emitting a sound through a transducer 106, and/or sending a message through the network 135 to, for example, an operations system (computer) 140 that is connected to the network 135. In such, the system for directly radiating skin 1 includes a network adapter or modem 130 to enable communication through the network 130 to, for example, an operations processor 140.

Being that it is difficult to discern which devices that emit ultraviolet radiation 70 has aged or failed because the devices that emit ultraviolet radiation 70 typically do not emit visible light and/or because it is harmful to expose one's eye to the light emitted by the devices that emit ultraviolet radiation 70, in some embodiments, separate current sensors 120 are configured in series with each of the devices that emit ultraviolet radiation 70 (not shown). In such, the processor 100 reads the current going to/from each of the devices that emit ultraviolet radiation 70 and the processor 100 indicates which device(s) that emit ultraviolet radiation 70 has aged or failed by eliminating the lamps/LEDs 104 in a certain pattern, colors, or sequence (e.g., blinking 3 times if the third device that emits ultraviolet 70 has failed) and/or encoding an indication of the failed devices that emit ultraviolet radiation 70 in a message that is sent through the network 135 to an operations system 140.

Also in this example, one or more sensors 90 and/or pressure sensors 25 are interfaced to the processor 100. Any known and/or future sensor 90/25 that detects proper placement is anticipated and is connected to the processor 100. In the examples shown in FIGS. 1-3, position sensors 7 are activated as the head 5 of the exemplary system for directly radiating skin 1 is pushed against the patient's body, for example using micro switches. There are many known proximity detectors, including pressure sensors 25 to detect pressure of the head 5 against the patient's body, ultrasonic distance sensor (sonar), skin continuity sensors, mechanical switches (e.g. coupled to the position sensors), ambient light detectors, cameras 15, etc.

The processor monitors the status of the sensor(s) 90/25 and enables or disables operation of the devices that emit ultraviolet radiation 70 through operation of a power switching device 115 (e.g. solid-state switch or relay). In such, it is also anticipated that the processor 100 illuminate one or more indicators 9 or LEDs to signal that the devices that emit ultraviolet radiation 70 are operating after detection of proper placement of the head 5 against the patient and after supplying power to the devices that emit ultraviolet radiation 70 through operation of the power switching device 115.

Once the processor 100 detects the proper placement of the head 5 against the patient, the processor 100 closes the power switching device 115, thereby illuminating the device(s) that emit ultraviolet radiation 70 for emission of the ultraviolet light onto the patient (e.g. at a location prior to or after an incision is made). In some embodiments, the processor 100 also illuminates one or more lamps/LEDs 9 to provide feedback to the technician that the sterilization process is in operation. In some embodiments, the processor 100 retains power to the devices that emit ultraviolet radiation 70 until it is detected that the technician has moved the head 5 away from the patient's body. In other embodiments, the processor 100 retains power to devices that emit ultraviolet radiation 70 for a fixed or settable length of time. In either embodiment, once the devices that emit ultraviolet radiation 70 are shut off, any lamps/LEDs 9 that were illuminated are extinguished to indicate to the user that the sterilization has stopped and it is safe to move the head 5. It is anticipated that, in some embodiments, a display 8 provides instructions and the technician operates the system for directly radiating skin 1 through a control panel 10, for example, a touch screen control panel or a keyboard, or any other known input device.

In some embodiments, operation of the system for directly radiating skin 1 is controlled by a foot control 13, for example, pressing the foot control 13 turns on the devices that emit ultraviolet radiation 70 and/or initiates a timer that turns on the devices that emit ultraviolet radiation 70 for a period of time.

In some embodiments, the system for directly radiating skin 1 includes one or more patient detectors 99 that are interfaced to the processor as known in the industry, for example through a Universal Serial Bus interface (USB), a serial interface such as RS-232 or RS-422, RS-485, wireless connection, etc. In such, the patient detectors 99 are, for example, bar code readers (e.g. QR code or any type of bar code), Radio Frequency Identification Device (RFID) readers, facial recognition devices, retinal scanning devices, fingerprint scanners, etc. In such, the system for directly radiating skin 1 communicates with the remote operations system to retrieve patient records related to the patient being treated and, in some embodiments, the patient records are used to make system settings controlling the operation of the system for directly radiating skin 1, for example, the emission power and/or the duration of emission.

The processor 100 initiates operation of the devices that emit ultraviolet radiation 70 through, for example, the power switching device 115 to start the reduction of pathogens in the exposed area of the patient's body. The processor indicates operation by, for example, illuminating one or more of the indicators 9 (e.g. LEDs), in some embodiments with a specific color, sequence, pattern, etc. In some embodiments, the processor terminates the ultraviolet emission through, for example, the power switching device 115 after a period of time, which is either predetermined globally, predetermined based upon the identification of the user as determined by the one or more patient detectors 99. It is anticipated that the processor 100 query the remote operations system 140 to obtain information regarding the amount of exposure time, user identities, passwords/pins, current environmental conditions, pathogen alerts, etc. it is also anticipated that the system for directly radiating skin 1 include one or more environmental sensors (not shown), coupled to the processor 100 such as temperature sensors and humidity sensors, etc.

In some embodiments, once the processor 100 terminates the ultraviolet emission, the processor notifies the user that the user of completion by, for example, illuminating or blanking one or more of the indicators 9 (e.g. LEDs), in some embodiments with a specific color, sequence, pattern, etc. Also, in some embodiments, a completion record is created for the user. The completion record is transmitted to the operations processor 140 through the network 135, stored in the memory 102 for later retrieval, etc.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A system for directly radiating skin comprising:
an enclosure;
one or more ultraviolet emitters housed in the enclosure and configured to selectively emit ultraviolet light from the enclosure onto a surface where the ultraviolet light produces ozone at the surface;
means for detecting the surface; and
means for connecting a source of power to the one or more ultraviolet emitters for a period of time responsive to the means for detecting the surface indicating that the enclosure is positioned against the surface;
wherein the means for detecting the surface comprises an ultrasonic distance measuring system.

2. The system for directly radiating the skin of claim 1, wherein the surface is skin.

3. The system for directly radiating the skin of claim 1, wherein the one or more ultraviolet emitters comprise one or more ultraviolet emitting tubes.

4. The system for directly radiating the skin of claim 1, wherein the one or more ultraviolet emitters comprise one or more ultraviolet light emitting diodes.

5. The system for directly radiating the skin of claim 1, wherein the means for detecting comprises one or more position sensors coupled to switches.

6. The system for directly radiating the skin of claim 1, wherein the means for detecting comprises a camera.

7. The system for directly radiating the skin of claim 1, wherein the one or more ultraviolet emitters are protected by a filter.

8. The system for directly radiating the skin of claim 7, wherein the filter comprises a material selected from fused silica and quartz glass.

9. A method of radiating skin comprising:
providing a system that selectively emits ultraviolet light, the system having one or more skin contact detectors;
placing the system that selectively emits ultraviolet light against skin, thereby the one or more skin contact detectors detecting contact with the skin;
enabling the system that selectively emits ultraviolet light, thereby the system emits the ultraviolet light and the ultraviolet light produces ozone at the skin;
delaying for a period of time; and
disabling the system that selectively emits ultraviolet light, thereby stopping emission of the ultraviolet light and stopping production of the ozone;
wherein the one or more skin contact detectors comprises an ultrasonic distance measurement device that detects proximity to the skin.

10. The method of claim 9, wherein the time period is from five to ten seconds.

11. The method of claim 9, wherein the one or more skin contact detectors comprises a camera that detects proximity to the skin.

12. The method of claim 9, wherein the one or more skin contact detectors comprise one or more position sensors coupled to switches.

13. A system for radiating skin comprising:
an enclosure;
one or more ultraviolet emitters housed in the enclosure and covered by a filter, the filter passing ultraviolet light from the one or more ultraviolet emitters, the one or more ultraviolet emitters configured to emit ultraviolet light from the housing, through the filters, and onto a surface of skin where ozone is produced by ultra violet light emitted from the one or more ultraviolet emitters;
means for detecting contact with the surface of the skin, the means for detecting contact prevents the one or more ultraviolet emitters from emitting the ultraviolet light until contact is made with the surface of the skin; and
a timer configured to connect a source of power to the one or more ultraviolet emitters for a period of time responsive to the means for detecting the surface indicating contact with the surface of the skin;
wherein the one or more skin contact detectors comprises an ultrasonic distance measurement device that detects proximity to the skin.

14. The system for directly radiating the skin of claim 13, wherein the one or more ultraviolet emitters comprise one or more ultraviolet emitting tubes.

15. The system for directly radiating the skin of claim 13, wherein the one or more ultraviolet emitters comprise one or more ultraviolet light emitting diodes.

16. The system for directly radiating the skin of claim 13, wherein the means for detecting comprises one or more position sensors coupled to switches.

17. The system for directly radiating the skin of claim 13, wherein the means for detecting comprises a camera.

18. The system for directly radiating the skin of claim 13, further comprising a shroud interfaced to the enclosure, the shroud made of a pliable material that seals against the surface of the skin, thereby preventing escape of the ultraviolet light from an area between the enclosure and the surface of the skin when the one or more ultraviolet emitters emit the ultraviolet light.

* * * * *